United States Patent
You et al.

(10) Patent No.: US 11,479,474 B2
(45) Date of Patent: Oct. 25, 2022

(54) COMPOSITE NANOPARTICLES AND METHOD OF PREPARING THE SAME

(71) Applicant: KOREA RESEARCH INSTITUTE OF STANDARDS AND SCIENCE, Daejeon (KR)

(72) Inventors: Eun-Ah You, Daejeon (KR); Wansun Kim, Daejeon (KR); Tae Geol Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 16/498,307

(22) PCT Filed: Oct. 23, 2018

(86) PCT No.: PCT/KR2018/011875
§ 371 (c)(1),
(2) Date: Sep. 26, 2019

(87) PCT Pub. No.: WO2020/075880
PCT Pub. Date: Apr. 16, 2020

(65) Prior Publication Data
US 2021/0331933 A1    Oct. 28, 2021

(30) Foreign Application Priority Data

Oct. 8, 2018 (KR) .................. 10-2018-0119979

(51) Int. Cl.
*C01G 7/00*    (2006.01)
*G01N 21/65*   (2006.01)
(Continued)

(52) U.S. Cl.
CPC .................. *C01G 7/00* (2013.01); *B82B 1/00* (2013.01); *B82B 1/008* (2013.01); *G01N 21/65* (2013.01);
(Continued)

(58) Field of Classification Search
CPC .............................. G01N 21/658; B82Y 40/00
See application file for complete search history.

(56) References Cited

U.S. PATENT DOCUMENTS

2016/0126329 A1* 5/2016 Vellaisamy ......... H01L 29/0673
257/325

FOREIGN PATENT DOCUMENTS

| JP | 2012-008144 A | 1/2012 |
| KR | 10-2012-0132668 A | 12/2012 |

(Continued)

OTHER PUBLICATIONS

KR101486697, machine translation. (Year: 2015).*
(Continued)

*Primary Examiner* — Robert A Vetere
(74) *Attorney, Agent, or Firm* — Knobbe Martens Olson & Bear LLP

(57) ABSTRACT

Provided is a method of preparing composite nanoparticles, which includes: a) preparing a metal nanocore having a nano-star shape from a first reaction solution in which a first metal precursor is mixed with a first buffer solution; b) fixing a Raman reporter in the metal nanocore; and c) forming a metal shell, which surrounds the nanocore in which the Raman reporter is fixed, from a second reaction solution in which the nanocore in which the Raman reporter is fixed, and a second metal precursor are mixed with a second buffer solution.

9 Claims, 4 Drawing Sheets

(51) Int. Cl.
- B82B 1/00 (2006.01)
- G01N 33/543 (2006.01)
- G01N 33/553 (2006.01)
- B82Y 30/00 (2011.01)
- B82Y 35/00 (2011.01)
- B82Y 40/00 (2011.01)

(52) U.S. Cl.
CPC ......... *G01N 21/658* (2013.01); *G01N 33/543* (2013.01); *G01N 33/54346* (2013.01); *G01N 33/553* (2013.01); *B82Y 30/00* (2013.01); *B82Y 35/00* (2013.01); *B82Y 40/00* (2013.01); *C01P 2004/03* (2013.01); *C01P 2004/30* (2013.01); *C01P 2004/64* (2013.01); *C01P 2004/80* (2013.01)

(56) References Cited

FOREIGN PATENT DOCUMENTS

| | | |
|---|---|---|
| KR | 10-2014-0101980 A | 8/2014 |
| KR | 10-1486697 B1 | 1/2015 |
| KR | 101486697 B1 * | 1/2015 |
| KR | 10-2016-0057710 A | 5/2016 |
| KR | 10-2020-0040072 A | 4/2020 |

OTHER PUBLICATIONS

Xu et al., "Preparation of Au—Ag coreshell nanoparticles and application of bimetallic sandwich in surface-enhanced Raman scattering (SERS)," 2004, Colloids and Surfaces 257-258, pp. 313-317. (Year: 2004).*

Grzelczak et al., "Shape control in gold nanoparticle synthesis," 2008, Chem. Soc. Reviews 37, pp. 1783-1791. (Year: 2008).*

Chen et al., "Fabrication of gold nanoparticles with different morphologies in HEPES buffer," 2010, Rare Metals, vol. 29, No. 2, p. 180. (Year: 2010).*

Mao et al., "A novel biosensor based on Au@Ag core-shell nanoparticles for sensitive detection of methylamphetamine with surface enhanced Raman scattering," Jul. 2018, Talanta 190, pp. 263-268. (Year: 2018).*

Tian et al., "Highly sensitive detection of exosomes by SERS using gold nanostar@Raman reporter@nanoshell structures modified with a bivalent cholesterol labeled DNA anchor," 2018, Analyst, 143, pp. 4915-4922. (Year: 2018).*

Notice of Allowance of corresponding Korean Patent Application No. 10-2018-0119979—5 pages (dated May 11, 2020).

Khlebtsov et al., "A New Type of SERS Tags: Au@Ag Core/Shell Nanorods with Embedded Aromatic Molecules", Nanotechnologies in Russia, vol. 12, Nos. 9-10—14 pages (2017).

Office Action of corresponding Korean Patent Application No. 10-2018-0119979—3 pages (dated Feb. 14, 2020).

Xu et al., "Preparation of Au—Ag coreshell nanoparticles and application of bimetallic sandwich in surface-enhanced Raman scattering (SERS)", Colloids and Surfaces A: Physicochem. Eng. Aspects—6 pages (2005).

Zhang et al., "Gold and silver nanoparticle monomers are non-SERS-active: a negative experimental study with silica-encapsulated Raman-reporter-coated metal colloids", Phys. Chem. Chem. Phys., Issue 17—9 pages (2015).

International Search Report of corresponding PCT Application No. PCT/KR2018/011875—4 pages (dated Jul. 8, 2019).

Written Opinion of the International Search Authority of corresponding PCT Application No. PCT/KR2018/011875—7 pages (dated Jul. 8, 2019).

* cited by examiner

【Figure 1】
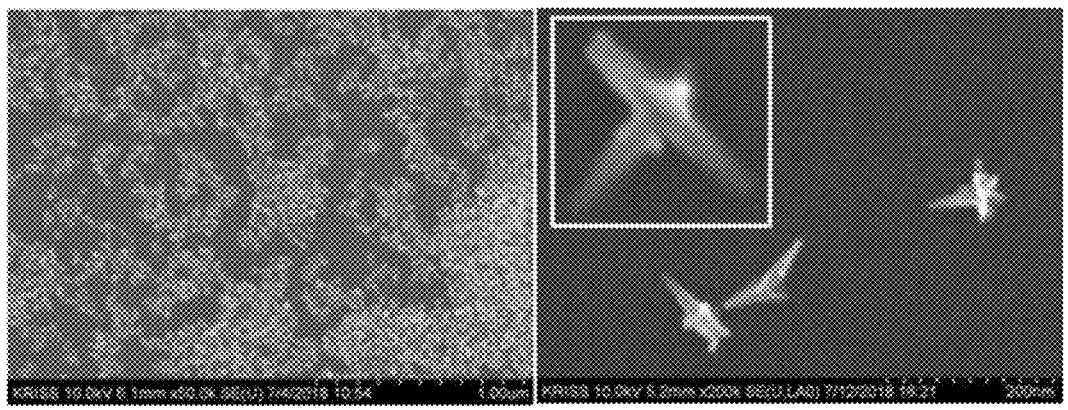
【Figure 2】
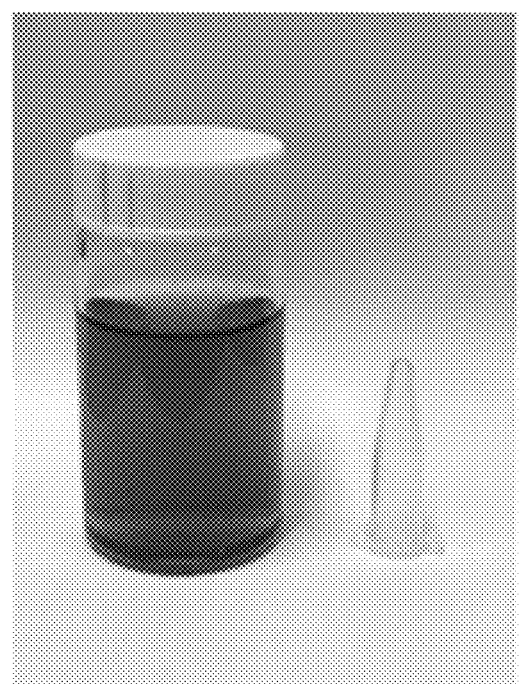

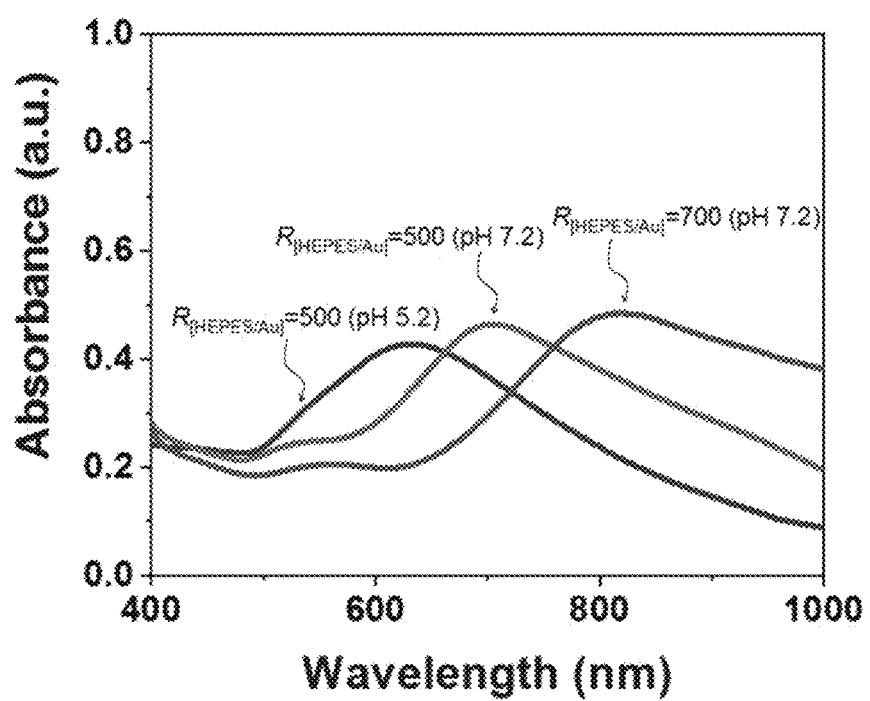
[Figure 3]

[Figure 4]
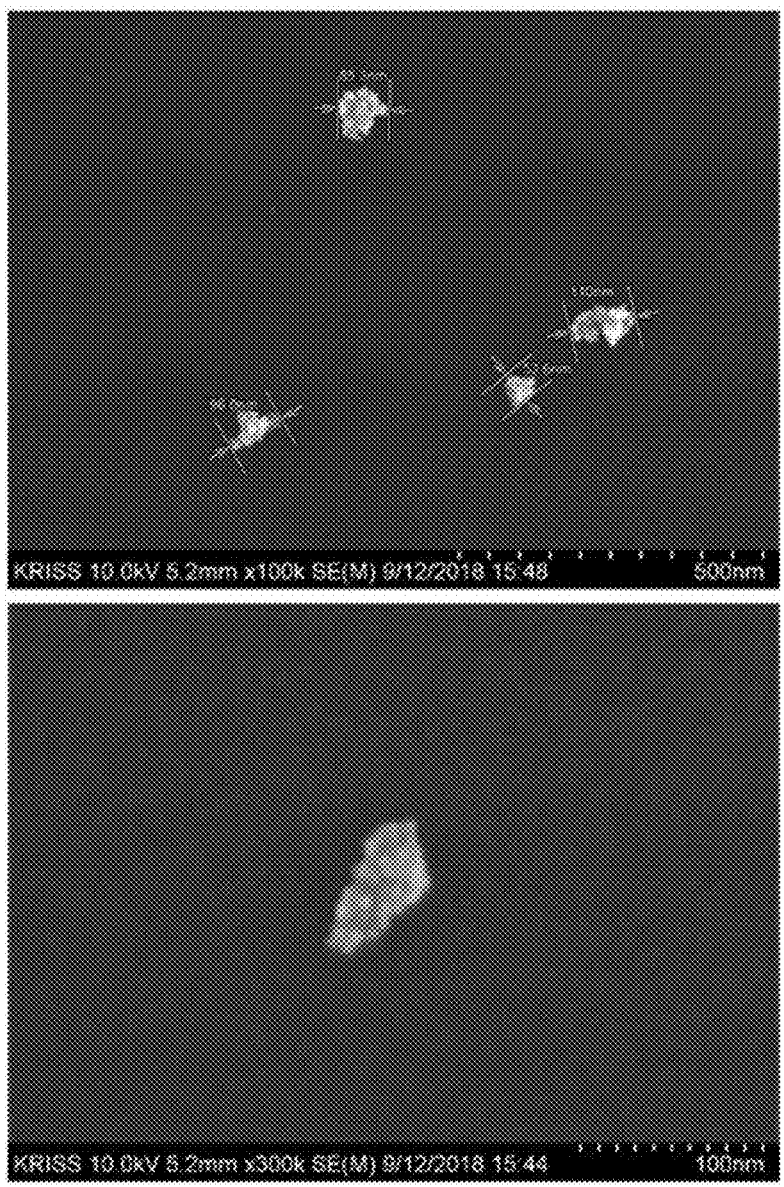

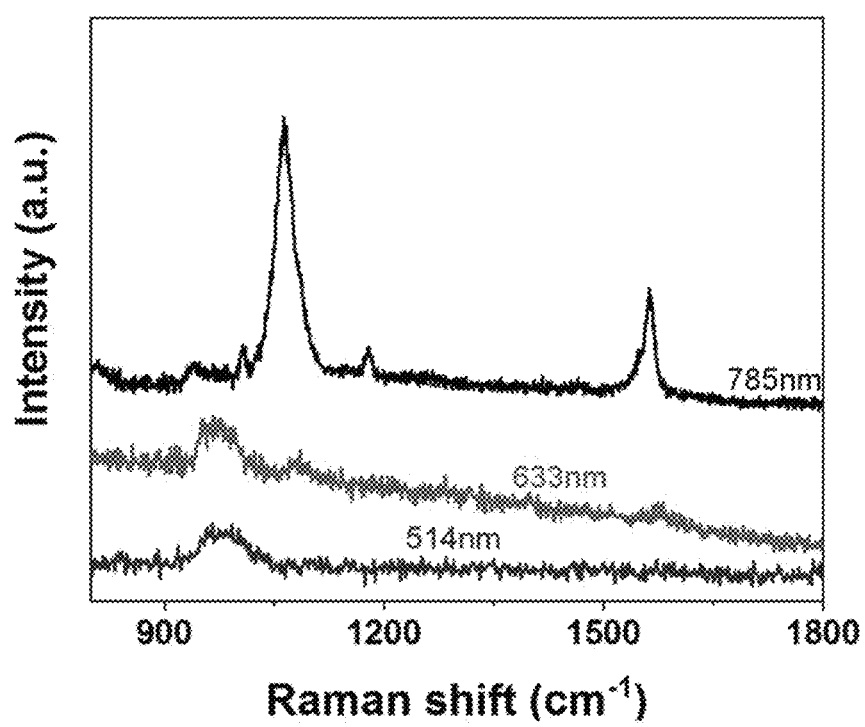
[Figure 5]

COMPOSITE NANOPARTICLES AND METHOD OF PREPARING THE SAME

TECHNICAL FIELD

The present invention relates to composite nanoparticles and a method of preparing the same, and more particularly, to biocompatible composite nanoparticles having a surface-enhanced Raman scattering activity and capable of being directly applied in vivo without any separate capping or pretreatment, and a method of preparing the same.

BACKGROUND ART

Surface-enhanced Raman scattering (hereinafter referred to as "SERS") spectrometry uses a phenomenon in which the intensity of Raman scattering greatly increases $10^6$ to $10^8$-fold or more when molecules are adsorbed onto a nanostructure surface of a metal such as gold, silver, and the like. This is high-sensitivity technology that may be combined with nanotechnology, which has currently developed very rapidly, to directly measure only one molecule, and particularly has been highly anticipated as being imperatively used as a medical sensor.

SERS spectrometry is a measuring technique having high selectivity and high informativity, and also is a potent analysis method for supersensitive chemical/biological/biochemical analysis. Thus, much research is being conducted to make early diagnosis of various diseases including Alzheimer's disease, diabetes, and the like, as well as high-sensitivity DNA analysis.

In addition, SERS spectroscopy-based biosensing and bioimaging are very useful for in vitro analysis as well as in vivo analysis (KR10-1845495) because it can detect both water-soluble and solid-phase samples with high sensitivity in a non-destructive manner and it can also detect extremely low concentrations of biochemicals with spatial resolution (having the order of several tens of micrometers) and temporal resolution (including real-time resolution).

However, development of SERS-active particles, which by themselves have hot spots, safely protect an organic constituent element including a Raman probe from external environments, can tune a localized surface plasmon resonance (LSPR) wavelength to a wide extent, and, among others, have biocompatibility, should be done preferentially to perform the SERS spectroscopy-based biosensing and bioimaging in vivo. Also, development of technology capable of mass-producing such SERS-active particles in a short period of time should be done preferentially to use the SERS-active particles for in vivo analysis in a real-time manner.

DISCLOSURE

Technical Problem

An object of the present invention is to provide composite nanoparticles having a surface-enhanced Raman scattering activity (hereinafter referred to a "SERS activity") and having biocompatibility, and a method of preparing the same.

Another object of the present invention is to provide SERS-active composite nanoparticles in which an organic matter including a Raman reporter is stably protected from external environments, and a method of preparing the same.

Still another object of the present invention is to provide SERS-active composite nanoparticles capable of generating remarkably improved Raman scattering signals because two or more different hot spots are positioned on the particles themselves, and a method of preparing the same.

Yet another object of the present invention is to provide SERS-active composite nanoparticles capable of tuning a localized surface plasmon resonance (LSPR) wavelength to a wide extent, and a method of preparing the same.

Yet another object of the present invention is to provide a preparation method capable of mass-producing the composite nanoparticles having biocompatibility and having excellent durability and high SERS activity in a short period of time.

Technical Solution

In one general aspect, a method of preparing composite nanoparticles according to the present invention includes: a) preparing a metal nanocore having a nano-star shape from a first reaction solution in which a first metal precursor is mixed with a first buffer solution; b) fixing a Raman reporter in the metal nanocore; and c) forming a metal shell, which surrounds the nanocore in which the Raman reporter is fixed, from a second reaction solution in which the nanocore in which the Raman reporter is fixed, and a second metal precursor are mixed with a second buffer solution.

In the method of preparing composite nanoparticles according to one embodiment of the present invention, each of the first reaction solution and the second reaction solution may not contain a surfactant.

In the method of preparing composite nanoparticles according to one embodiment of the present invention, a shape, a size, or both the shape and the size of the nanocore may be adjusted by controlling one or more factors selected from a molar ratio of the first metal precursor to a first buffer agent of the first buffer solution; and a pH of the first buffer solution.

In the method of preparing composite nanoparticles according to one embodiment of the present invention, a molar ratio R1 obtained by dividing the number of moles of the first buffer agent by the number of moles of the first metal precursor may be in a range of 200 to 750.

In the method of preparing composite nanoparticles according to one embodiment of the present invention, a molar ratio R2 obtained by dividing the number of moles of the second buffer agent of the second buffer solution by the number of moles of the second metal precursor may be in a range of 100 to 400.

In the method of preparing composite nanoparticles according to one embodiment of the present invention, each of the first buffer solution and the second buffer solution may contain one or more selected from 4-(2-hydroxyethyl)-1-piperazineethane sulfonic acid (HEPES), 4-(2-hydroxyethyl)piperazine-1-ethane sulfonic acid (MES), phosphated buffered saline (PBS), tris(2-amino-2-hydroxymethyl propane-1,3-idol), phosphate buffer (PB), 3-(N-morpholino) propane sulfonic acid (MOPS), 3-[[1,3-dihydroxy-2-(hydroxymethyl)propan-2-yl]amino]propane-1-sulfonic acid (TAPS), and piperazine-N,N'-bis(2-ethane sulfonic acid) (PIPES).

In the method of preparing composite nanoparticles according to one embodiment of the present invention, a metal of the metal precursor may be Au or Ag.

The method of preparing composite nanoparticles according to one embodiment of the present invention may further include, after the forming of the metal shell from the second reaction solution: d) fixing a receptor, which binds to an analyte, in the metal shell.

In the method of preparing composite nanoparticles according to one embodiment of the present invention, the composite nanoparticles may be used in vivo.

In another general aspect, there are provided composite nanoparticles prepared by the method of preparing composite nanoparticles as described above.

In still another general aspect, composite nanoparticles according to the present invention include: metal nanocore having a nano-star shape; a self-assembled monolayer including a Raman reporter fixed in the metal nanocore; and a metal shell surrounding the self-assembled monolayer.

In the composite nanoparticles according to one embodiment of the present invention, the composite nanoparticles may have a metal surface originating from the metal shell.

In the composite nanoparticles according to one embodiment of the present invention, the metal nanocore may include a central region having a size of 10 to 50 nm and protrusions having a size of 5 to 70 nm and protruding from the central region to taper in a protruding direction.

In the composite nanoparticles according to one embodiment of the present invention, the metal shell may be composed of fine metal particles having an average size of 1 to 5 nm, and may have irregular unevenness formed by coagulation of the fine metal particles.

In the composite nanoparticles according to one embodiment of the present invention, the composite nanoparticles may further include a receptor fixed in the metal shell to bind to an analyte.

In the composite nanoparticles according to one embodiment of the present invention, the composite nanoparticles may be used in vivo.

In yet another general aspect, a surface-enhanced Raman scattering (SERS) nanoprobe includes the composite nanoparticles as described above.

Advantageous Effects

The composite nanoparticles according to the present invention have an advantage in that the composite nanoparticles have biocompatibility because the composite nanoparticles are free from a surfactant during or right after the preparation of the composite nanoparticles, and also have an advantage in that the composite nanoparticles can be directly used in in vivo without any separate post-treatment processes.

Also, the composite nanoparticles according to the present invention have an advantage in that an analyte can be analyzed by means of irradiation with near-infrared rays because the composite nanoparticles have a very wide tuning range of LSPR wavelengths (including a region of 800 nm).

In addition, the composite nanoparticles according to the present invention have advantages in that, because the composite nanoparticles include a metal nanocore having a nano-star shape, the strong hot spots may be positioned in the nanoparticles themselves, and a nanogap (a hot spot) having a uniform size can be formed between the metal nanocore and the metal shell over the entire region of the composite nanoparticles, and also have an advantage in that the metal shell itself can have a nanogap formed by surface unevenness, and the very high enhancement of Raman signals can also be realized when a Raman reporter is positioned in the nanogap (i.e., hot spot).

Additionally, the composite nanoparticles according to the present invention have an advantage in that the composite nanoparticles have very excellent durability and physical/chemical stability because an organic component including the Raman reporter is surrounded by the metal shell so that the organic component is protected by the metal shell, and the metal nanocore, the self-assembled monolayer of the Raman reporter, and the metal shell are strongly bound to each other via two functional groups of the Raman reporter.

Further, the method of preparing composite nanoparticles according to the present invention has an advantage in that the composite nanoparticles having the aforementioned advantages can be mass-produced without any aid of surfactants at room temperature in a short period of time using highly simple methods.

DESCRIPTION OF DRAWINGS

FIG. 1 is a scanning electron microscope image for observing a metal nanocore prepared according to one embodiment of the present invention.

FIG. 2 is an optical image for observing an Au nanocore dispersion dispersed in a HEPES buffer solution.

FIG. 3 is a graph for measuring the optical absorbance of the metal nanocore prepared according to one embodiment of the present invention.

FIG. 4 is a scanning electron microscope image for observing composite nanoparticles prepared according to one embodiment of the present invention.

FIG. 5 is a graph showing the surface-enhanced Raman scattering (SERS) spectrum of the composite nanoparticles prepared according to one embodiment of the present invention.

BEST MODE

Hereinafter, composite nanoparticles according to the present invention and a method of preparing the same will be described in detail with reference to the accompanying drawings. The drawings presented hereinbelow are shown as one example to sufficiently provide the scope of the present invention to those skilled in the art. Therefore, it should be understood that the present invention may be embodied in various forms, but is not intended to be limiting in the drawings presented hereinbelow. In this case, the drawings presented hereinbelow may be shown in an exaggerated manner to make the scope of the present invention more clearly apparent. In this case, unless otherwise defined, the technical and scientific terms used herein have the same meaning as commonly understood by one of ordinary skill in the art to which the present invention pertains. In the following description and the accompanying drawings, a description of known functions and configurations, which may unnecessarily obscure the subject matter of the present invention, will be omitted. Unless otherwise particularly defined, in the following context, the term "solution" refers to an aqueous solution including deionized water, and the term "concentration" refers to a molar concentration.

A method of preparing composite nanoparticles according to the present invention includes: a) preparing a metal nanocore having a nano-star shape from a first reaction solution in which a first metal precursor is mixed with a first buffer solution; b) fixing a Raman reporter in the metal nanocore; and c) forming a metal shell, which surrounds the nanocore in which the Raman reporter is fixed, from a second reaction solution in which the nanocore in which the Raman reporter is fixed, and a second metal precursor are mixed with a second buffer solution.

In this case, the nano-star shape may be a shape including a single central region and one or more protrusions, particularly two or more, more particularly 2 to 10, and further particularly 3 to 8 protrusions which protrude from the central region to taper in a protruding direction. The specific shape of the protrusions may be a polypyramidal or conical shape, and the like, but the present invention is not particularly limited thereto. When the metal nanocore has two or more protrusions, the shapes or sizes (protruding lengths) of the respective protrusions may be the same as or different from each other. When the metal nanocore has two or more protrusions, the two or more protrusions may have a symmetric relation with respect to the central region, may have a constant angle formed with each other, or may have protrusions protruding from the central region in random positions.

To prepare the metal nanoparticles and design the shapes of the metal nanoparticles, as known in the art, an organic surfactant capable of inhibiting growth of the metal nanoparticles or inducing the growth of the metal nanoparticles in a certain direction while providing the metal nanoparticles with a proper reducing property, and/or stabilizing the nanoparticles may be used as well-known and widely used in the art. In this case, an organic acid is used in combination with the organic surfactant, or an organic acid capable of replacing the surfactant is used. However, an organic surfactant harmful to the living body, or the organic surfactant and an organic acid-derived organic matter are bound to the metal nanoparticles synthesized by such a method. Therefore, a post-treatment process of capping the particles with a capping material having biocompatibility or replacing a harmful surface functional group of the organic surfactant, and the like with another functional group having biocompatibility is essentially required for use in vivo.

However, the capping using the capping material has a drawback in that the capping may significantly reduce the SERS spectroscopy-based biosensing or bioimaging intensity, and also has a drawback in that, when the organic surfactant is intended to be replaced with a biocompatible functional group, the capping requires the organic surfactant binding to a metal material with very strong binding affinity so as to inhibit the growth of the particles or induce the growth of the particles in a certain direction, which makes it difficult to achieve the complete replacement of the organic surfactant, resulting in residual toxicity.

In the method of preparing composite nanoparticles according to the present invention as described above, because the metal nanocore and the metal shell are already formed from the buffer solution having biocompatibility and the solution containing the metal precursor, respectively, the prepared composite nanoparticles are free from the organic surfactant harmful to the living body, and thus may have biocompatibility immediately after preparation of the composite nanoparticles.

That is, the method of preparing composite nanoparticles according to the present invention has an advantage in that the composite nanoparticles having biocompatibility may be prepared, which may be injected in a state in which the composite nanoparticles are prepared without any separate post-treatment process.

Therefore, in the method of preparing composite nanoparticles according to one embodiment of the present invention, each of the first reaction solution and the second reaction solution may not contain a surfactant (i.e., an organic surfactant). In addition, each of the first reaction solution and the second reaction solution may not contain both a surfactant and an organic acid.

Also, the method of preparing composite nanoparticles according to the present invention has an advantage in that the composite nanoparticles may be mass-produced at low cost in a short period of time because the composite nanoparticles are prepared using a simple process, which includes forming a metal nanocore using a solution containing a buffer solution and a metal precursor, attaching a Raman reporter, and forming a metal shell using the solution containing the buffer solution and the metal precursor. The preparation method according to the present invention capable of mass-producing the biocompatible nanoparticles immediately after the composite nanoparticles are prepared at low cost using a simple process is very suitable for in vivo applications which require a remarkably large amount of the composite nanoparticles.

In addition, the method of preparing composite nanoparticles according to the present invention has an advantage in that an organic matter including the Raman reporter may be stably protected from external environments because the organic matter including the Raman reporter is not exposed to surfaces of the composite nanoparticles and is surrounded by the metal shell.

Furthermore, the method of preparing composite nanoparticles according to the present invention has an advantage in that the composite nanoparticles themselves can enhance scattering signals because a hot spot is formed in the metal nanocore itself when the metal nanocore has a nano-star shape.

In this case, as known in the art, the hot spot refers to a region in which a very strong local electric field is formed and localized surface plasmon resonance (LSPR) is generated.

When the signals are enhanced by hot spots between two separate constituent elements, such as between the nanoparticles, between the nanoparticles and other constituent elements, or the like, the signals may be enhanced even when an analyte is positioned in (or bound to) a nanogap region between two constituent elements or regions around the nanogap region. Such a spatial constraint limits the size of the analyte, thereby making it impossible to analyze a biochemical material having a size of several or several tens of micrometers.

However, when each of single composite nanoparticles in an individually separated state itself has a hot spot, the signals may be enhanced merely by allowing the analyte to bind to the composite nanoparticles. Therefore, the single composite nanoparticles are very suitable for in vivo detection/analysis of various biochemical materials because there are no substantial limitations on the size of the analyte.

Also, the method of preparing composite nanoparticles according to the present invention has an advantage in that, when the metal nanocore has a nano-star shape, the LSPR wavelength may be tuned to a very wide extent by adjusting a spherical shape or size (including the length of a protruding branch, or the like) of a nano-star. As one specific example, when the metal nanocore has a nano-star shape, the LSPR wavelength may also be tuned to a wavelength range of 800 nm at which the LSPR wavelength may not be tuned in a spherical shape. By the LSPR wavelength which may be tuned to this wavelength range of 800 nm or more, it may be meant that the detection and analysis of the analyte may be achieved through irradiation with light having a band of near-infrared rays (NIR, 780 nm to 1,500 nm) rather than a band of visible rays.

When a biomaterial including the biochemical material is irradiated with visible rays, as known in the art, a fluorescence phenomenon may occur. Because the intensity of fluorescence is much stronger than that of Raman scattering, and the fluorescence occurs in a region similar to that of Raman scattering, the Raman spectrum may overlap with fluorescence peaks, which makes it difficult to obtain the pure Raman spectrum. Therefore, the SERS analysis through irradiation with light having a band of near-infrared rays rather than visible rays is very favorable in the field of biology because the Raman spectrum may be obtained without any effect (interference) of fluorescence.

The shape, the size, or both the shape and the size of the metal nanocore may be adjusted by controlling one or more factors selected from the molar ratio of the first metal precursor to a first buffer agent of the first buffer solution, and the pH of the first buffer solution. In this case, it is reasonable that the first buffer solution may contain a conventional inorganic acid such as HCl, or the like, a conventional inorganic base such as NaOH, or the like, and a mixture thereof in order to regulate the pH of the first buffer solution. The pH regulation using such an inorganic acid or an inorganic base is favorable because the inorganic acid or base does not react with the prepared metal nanocore so that the inorganic acid or base cannot cause damage to biocompatibility.

As one specific example, the molar ratio R1 obtained by dividing the number of moles of the first buffer agent in the first reaction solution by the number of moles of the first metal precursor may be in a range of 200 to 750. The metal nanocore having a nano-star shape may be prepared in this R1 range. That is, the metal nanocore having a nano-star shape, which has a central region having a size of 10 to 50 nm, and particularly a size of 10 to 40 nm, may be prepared.

Favorably, R1 may be in a range of 500 to 750. When R1 is controlled to 500 to 750, the metal nanocore having a nano-star shape, which includes 3 or more protrusions, and particularly 3 to 8 protrusions, may be prepared, wherein the protrusions have a size of 5 to 70 nm, particularly 5 to 50 nm, and more particularly 10 to 50 nm.

Also, when the R1 is controlled in a range of 200 to 750, the lengths of the protrusions (i.e., extrusions or branches) protruding from the central region of the metal nanocore may be adjusted. As one more specific example, the lengths of the protrusions may be extended by increasing an R1 value in a range of 200 to 750. In this case, the LSPR wavelength of the composite nanoparticles (or a metal nanocore) may be adjusted by adjusting the lengths of the protrusions. In this case, the LSPR wavelength may be adjusted to 600 to 900 nm by adjusting the R1 in a range of 200 to 750.

The lengths of the protrusions protruding from the central region of the metal nanocore may be adjusted by regulating the pH of the first buffer solution, in connection with R1 or independently from of R1 (under constant R1 conditions). Specifically, the pH of the first buffer solution may be in a range of 5.0 to 7.5, and the lengths of the protrusions may increase by raising the pH of the first buffer solution.

The first buffer solution (or a first buffer agent) may contain one or more selected from 4-(2-hydroxyethyl)-1-piperazineethane sulfonic acid (HEPES), 4-(2-hydroxyethyl)piperazine-1-ethane sulfonic acid (MES), phosphated buffered saline (PBS), tris(2-amino-2-hydroxymethyl propane-1,3-idol), phosphate buffer (PB), 3-(N-morpholino) propane sulfonic acid (MOPS), 3-[[1,3-dihydroxy-2-(hydroxymethyl)propan-2-yl]amino]propane-1-sulfonic acid (TAPS), and piperazine-N,N'-bis(2-ethane sulfonic acid) (PIPES). Such a buffer agent may serve as a weak reducing agent for reducing a metal, may not require a surfactant for promoting stabilization of the prepared metal nanocore, and may secure the biocompatibility of the metal nanocore. In this case, as described above, it is reasonable that the first buffer solution (i.e., an aqueous solution) may further contain an inorganic acid and/or an inorganic base to regulate the pH.

The first metal of the first metal precursor may be a metal that generates surface plasmons by means of interaction with light. As a specific example, the first metal may include gold, silver, platinum, palladium, nickel, aluminum, copper, or a mixture or an alloy thereof. However, the first metal may be gold or silver in consideration of the in vivo stability. In the first metal according to one favorable example, the first metal precursor may be a gold precursor such as $HAuCl_4$, $HAuBr_4$, $NaAuCl_4$, $AuCl_3 \cdot 3H_2O$, $NaAuCl_4 \cdot 2H_2O$, or a mixture thereof, or may be a silver precursor such as $AgNO_3$, or the like. However, it is reasonable that the present invention is not limited to the types of spherical materials of the metal precursor.

More particularly, the step a) may include mixing a first metal precursor solution with a first buffer solution to prepare a first reaction solution, and reacting the first reaction solution at a temperature of 15 to 40° C. to prepare a metal nanocore.

A molar concentration of the first buffer agent in the first buffer solution may be in a range of 100 to 400 mM, and a molar concentration of the first metal precursor in the first metal precursor solution may be in a range of 20 to 60 mM. When the first buffer solution and the first metal precursor solution having such molar concentrations are used, it is favorable that most of the first metal precursor added may be converted into the metal nanocore, and the reaction (synthesis of the metal nanocore) may be completed in a reaction time of 10 to 50 minutes. However, the concentration of the first buffer solution and the concentration of the first metal precursor solution are not particularly limited to these concentration ranges as described above. When the first metal precursor solution is mixed with the first buffer solution, it is reasonable that the solutions may be mixed to satisfy the R1 value as described above.

The reaction may proceed concurrently with mixing of the first metal precursor solution with the first buffer solution. In this case, the reaction may be performed at a temperature of 15 to 40° C., particularly a temperature of 15 to 35° C., more particularly a temperature of 15 to 25° C., and further particularly room temperature (21 to 23° C.). In this case, it is reasonable that the room temperature may refer to a temperature in a state in which heat energy is not artificially applied to the first reaction solution. The reaction time may be suitable as long as it is a sufficient time to complete synthesis of the metal nanocore. As a specific example, the reaction time may be in a range of 10 to 50 minutes, and more specifically 20 to 40 minutes, but the present invention is not limited thereto.

If any, the first reaction solution may be optionally stirred during reaction of the first reaction solution. When the reaction solution is stirred, the reaction yield may be improved, but the shape or size of the prepared metal nanocore may be slightly affected by the stirring conditions. The stirring is sufficient as long as the stirring rate is in a range of approximately 500 rpm to 1,500 rpm.

Also, the step a) may include: a1) mixing the first metal precursor solution with the first buffer solution to prepare a first reaction solution and reacting the first reaction solution at a temperature of 15 to 40° C. to prepare a metal nanocore; and a2) storing the first reaction solution whose reaction has been completed as a dispersion medium or stock solution for the metal nanocore at a temperature of 1 to 10° C., and particularly a temperature of 1 to 5° C. That is, after the reaction of a1) is completed, the metal nanocore may be stored in a state of the first reaction solution containing the metal nanocore without being separated and recovered from the first reaction solution whose reaction has been completed. In this case, the metal nanocore may be stored at a low temperature of 1 to 10° C., and particularly a low temperature of 1 to 5° C. On the other hand, the step a) may optionally include: a1) mixing the first metal precursor solution with the first buffer solution to prepare a first reaction solution and reacting the first reaction solution at a temperature of 15 to 40° C. to prepare a metal nanocore; and a2) recovering the metal nanocore from the first reaction solution whose reaction has been completed and dispersing the metal nanocore in a first buffer solution (a separate first buffer solution) to store the metal nanocore dispersion at a temperature of 1 to 10° C., and particularly a temperature of 1 to 5° C.

When the metal nanocore prepared in the step a1) is stored at a low temperature of 1 to 10° C. using the reaction solution or first buffer solution whose reaction has been completed as a dispersion medium other than the dispersion medium including water, plasmonic-active characteristics of the metal nanocore may be stably retained without any change in the plasmonic-active characteristics even when the metal nanocore is stored for several tens of days.

In this case, as described above, the first reaction solution may not contain a surfactant, which may serve as a reducing agent and may simultaneously improve stabilization and dispersing properties of the nanoparticles as well, an organic acid, or both the surfactant and the organic acid. In this case, the step a1) may be performed using only the first buffer solution and the first metal precursor solution. As such, the preparation method according to the present invention is very suitable for mass production of the metal nanocore because the metal nanocore may be synthesized by simply mixing the two solutions and reacting the resulting mixture at room temperature for several tens of minutes.

After the step a) is performed, the fixing of the Raman reporter in the metal nanocore (step b)) may be performed.

The Raman reporter may refer to an organic compound (i.e., an organic molecule) that includes a Raman-active molecule, and may refer to an organic compound (i.e., an organic molecule) that has a binding affinity for a metal of the metal nanocore and includes a Raman-active molecule. Any of the Raman reporters may be used without limitation as long as the Raman reporters are already known and widely used in the related art.

When the Raman reporter (a molecule) has a binding affinity for the metal of the metal nanocore, a self-assembled monolayer of the Raman reporter may be formed on the metal nanocore to which a bare surface of the metal is exposed.

As known in the art, when the nanoparticles are synthesized using the organic surfactant or the organic acid, organic functional groups derived from the organic surfactant or the organic acid are bound to surfaces of the synthesized metal nanoparticles with very strong binding affinity. Therefore, it may be difficult to uniformly and completely cover (replace) the surfaces of the metal nanoparticles with a desired functional group due to the functional groups already strongly bound to the surfaces of the metal nanoparticles.

However, in the step a), the metal nanocore is entirely prepared from the buffer solution and the metal precursor in a state in which the organic acid or the organic surfactant is excluded. As described above, when the dispersion is stably retained in the buffer solution, the prepared metal nanocore may purely have a surface state of the metal itself. Owing to such a surface state of the metal, the Raman reporter (i.e., an organic compound having a binding affinity for the metal nanocore and including a Raman-active molecule) is spontaneously bound to the metal nanocore in a uniform and homogeneous fashion. Even when the metal nanocore has a shape with high unevenness, which is referred to as a "nano-star", the self-assembled monolayer of the Raman reporter may be stably formed.

The Raman-active molecule may include a surface-intensified Raman-active molecule, a surface-enhanced resonance Raman-active molecule, a Hyper Raman-active molecule, or a Coherent anti-Stokes Raman-active molecule. The Raman-active molecule may have Raman signals and fluorescence signals at the same time, or may have Raman signals.

As a specific example, the Raman-active molecule may be selected from the group consisting of cyanine, fluorescein, rhodamine, 7-nitrobenz-2-oxa-1,3-diazole (NBD), phthalic acid, terephthalic acid, isophthalic acid, cresyl fast violet, cresyl blue violet, brilliant cresyl blue, para-aminobenzoic acid, erythrosine, biotin, digoxigenin, phthalocyanine, azomethine, xanthine, N,N-diethyl-4-(5'-azobenzotriazolyl)-phenylamine, aminoacridine, and a combination thereof. Examples of the cyanine may include Cy3, Cy3.5, or Cy5. Examples of the fluorescein may include carboxyfluorescein (FAM), 6-carboxy-2',4,4',5',7,7'-hexachlorofluorescein (HEX), 6-carboxy-2',4,7,7'-tetrachlorofluorescein (TET), 5-carboxy-4',5'-dichloro-2',7'-dimethoxy fluorescein, 6-carboxy-4',5'-dichloro-2',7'-dimethoxyfluorescein (Joe), 5-carboxy-2',4',5',7'-tetrachlorofluorescein, 5-carboxyfluorescein, or succinyl fluorescein. Examples of the rhodamine may include tetramethylrhodamine (Tamra), 5-carboxyrhodamine, 6-carboxyrhodaminerhodamine, 6G (Rhodamine 6G: R6G), tetramethyl rhodamine isothiol (TRIT), sulforhodamine 101 acid chloride (Texas Red dye), carboxy-X-rhodamine (Rox), or rhodamine B.

As another specific example, the Raman-active molecule may be a Raman-active molecule in the form of a benzene ring, and the Raman-active molecule in the form of a benzene ring may include 4-aminothiophenol (4-ATP), 4-mercaptobenzoic acid (4-MBA), phenyl isothiocyanate (PITC), benzenethiol (BT), 1,4-benzenedithiol (BDT), biphenyl-4,4'-dithiol (BPDT), p-terphenyl-4,4"-dithiol (TPDT), 4-bromobenzenethiol (4-BBT), 4-chlorobenzenethiol (4-CBT), 3,3'-diethylthiatricarbocyanine iodide (DTIC), and the like.

However, when the nanogap (hot spot) between the metal nanocore and the metal shell is formed by the Raman reporter bound to the metal nanocore, the length (size) of the Raman reporter may be less than or equal to 3 nm, and particularly in a range of 0.5 to 2 nm in terms of the formation of the hot spot in which signals are more strongly enhanced.

Also, the Raman reporter includes a Raman-active molecule, wherein the Raman-active molecule may have a first functional group spontaneously binding to the first metal. More favorably, the Raman-active molecule may have a first functional group spontaneously binding to the first metal and a second functional group spontaneously binding to the second metal (a second metal of the second metal precursor). In the step c), when the metal shell is formed, it is favorable that the second functional group may provide a nucleation site for a more smooth and uniform second metal shell, and remarkably improve the binding affinity between the second metal shell and the metal nanocore in which the Raman reporter is fixed.

The functional group (the first or second functional group) may be suitable in consideration of the metal as long as the functional group is a functional group known to spontaneously bind to the corresponding metal. As one specific example, when the first metal and the second metal are each independently gold or silver, the functional group (the first or second functional group) may be a thiol group (—SH), a carboxyl group (—COOH), an amine group (—NH$_2$), or the like, but the present invention is not limited to the specific types of the functional group.

When the Raman-active molecule having a binding affinity for the metal of the metal nanocore is spontaneously bound to (fixed in) the metal nanocore via the first functional group, the self-assembled monolayer of the Raman reporter may be formed on the metal nanocore.

The formation of such a self-assembled monolayer may allow a film of the Raman reporter having a uniform thickness to be homogeneously formed on the entire surface of the metal nanocore although the nano-star shape of the metal nanocore is a shape having high anisotropy.

The step b) of fixing the Raman reporter in the metal nanocore may include preparing a mixed solution containing the Raman reporter and the metal nanocore prepared in the step a) and stirring the mixed solution using ultrasonic waves.

Specifically, the step b) may include: b1) mixing the metal nanocore prepared in the step a) and the Raman reporter so that the molar concentrations of the metal nanocore and the Raman reporter are in a range of 0.01 to 1 nM and 10 to 1,000 µM, respectively, to prepare a mixed solution; reacting the mixed solution at room temperature for 10 to 30 minutes while stirring using ultrasonic waves; and b4) separating and recovering the metal nanocore in which the Raman reporter is fixed. In this case, the mixed solution may be an aqueous mixed solution. In this case, the mixed solution may further include a water-soluble phosphorus-based aromatic compound such as bis(p-sulfonatophenyl) phenylphosphine (BSPP), and the like in order to prevent coagulation of the metal nanocore.

After the step b) is performed, the step c) of forming the metal shell, which surrounds the nanocore in which the Raman reporter is fixed, from the second reaction solution, in which the nanocore in which the Raman reporter is fixed and the second metal precursor are mixed with the second buffer solution, may be performed. The nanocore (a metal nanocore) in which the Raman reporter is fixed may be a metal nanocore in which the self-assembled monolayer of the Raman reporter is formed.

In the step c), the molar ratio (a molar ratio R2 obtained by dividing the number of moles of the second buffer agent by the number of moles of the second metal precursor) of the second metal precursor to the second buffer agent of the second buffer solution may be in a range of 100 to 400, and desirably in a range of 200 to 400. A metal shell (a shell of the second metal) may be formed in the form of a thin film having a thickness of 5 to 20 nm, which stably covers the Raman reporter fixed in the metal nanocore, may be formed by adjusting the R2 to 100 to 400, and desirably 200 to 400. In this case, it is reasonable that the pH of the second buffer solution may be in a range of pH 6.0 to 7.5, and the second buffer solution may contain a conventional inorganic acid such as HCl, or the like, a conventional inorganic base such as NaOH, or the like, and a mixture thereof in order to regulate the pH of the second buffer solution.

The metal shell formed in the step c) has an advantage in that, when a nanogap between the metal shell and the metal nanocore is formed by the Raman reporter fixed in the nanocore, the hot spot is not formed in the form of a dot or line but formed in a plane form corresponding to a surface of the metal nanocore, thereby obtaining stronger Raman scattering signals. Also, when the size of the nanogap is determined by the self-assembled monolayer of the Raman reporter, the self-assembled monolayer may be formed with the Raman reporter simply designed to have a proper size, thereby controlling the size of the nanogap over the entire region of a nano-star uniformly and precisely.

Also, the metal shell, which is composed of fine metal (second metal) particles having an average size of 1 to 5 nm and has irregular unevenness due to coagulation of the fine metal particles, may be formed by adjusting the R2 to 100 to 400, and desirably 200 to 400.

Very fine metal particles having an average size of 1 to 5 nm is advantageous in that a thin metal shell may be formed with the Raman reporter, particularly a self-assembled monolayer interposed therebetween while stably and compactly surrounding the nanocore having a shape having high anisotropy. Also, the coagulation between the fine metal particles and the irregular unevenness caused by the coagulation may be more advantageous in terms of signal enhancement because a hot spot may be formed on a surface of the shell itself, and hot spots may also be formed by the metal nanocore having a nano-star shape and by the nanogap between the metal nanocore and the metal shell.

Apart from the first buffer solution, the second buffer solution (or a second buffer agent) may contain one or more selected from 4-(2-hydroxyethyl)-1-piperazineethane sulfonic acid (HEPES), 4-(2-hydroxyethyl)piperazine-1-ethane sulfonic acid (MES), phosphated buffered saline (PBS), tris(2-amino-2-hydroxymethyl propane-1,3-idol), phosphate buffer (PB), 3-(N-morpholino)propane sulfonic acid (MOPS), 3-[[1,3-dihydroxy-2-(hydroxymethyl)propan-2-yl]amino]propane-1-sulfonic acid (TAPS), and piperazine-N,N'-bis(2-ethane sulfonic acid) (PIPES). Such a buffer agent may serve as a weak reducing agent for reducing a metal, may not require a surfactant for promoting stabilization of the prepared composite nanoparticles, and may secure the biocompatibility of the composite nanoparticles (i.e., the Raman reporter-fixed metal nanocore having a metal shell formed therein).

The second metal of the second metal precursor may also be a metal that generates surface plasmons by means of interaction with light, and the second metal may include gold, silver, platinum, palladium, nickel, aluminum, copper, or a mixture or an alloy thereof. However, aside from the first metal, the second metal may be gold or silver in consideration of the in vivo stability. In the second metal according to one favorable example, the second metal precursor may be a gold precursor such as HAuCl$_4$, HAuBr$_4$, NaAuCl$_4$, AuCl$_3$.3H$_2$O, NaAuCl$_4$.2H$_2$O, or a mixture thereof, or may be a silver precursor such as AgNO$_3$, or the like, but the present invention is not limited thereto.

More specifically, the step c) may include mixing a second buffer solution, a second metal precursor solution, and a metal nanocore dispersion in which the Raman reporter is fixed to prepare a second reaction solution, and reacting the second reaction solution at a temperature of 15 to 40° C., and favorably at room temperature for less than 20 minutes, particularly less than 10 minutes, and more particularly 5 to 10 minutes to prepare a metal shell. In this case, the violent stirring may be performed during the reaction, and the reaction may be terminated by adding an excessive amount of water to the second reaction solution.

The molar concentration of the second buffer agent in the second buffer solution may be in a range of 50 to 200 mM, the molar concentration of the second metal precursor in the second metal precursor solution may be in a range of to 20 mM, and the molar concentration of the metal nanocore in the metal nanocore dispersion in which the Raman reporter is fixed may be in a range of 0.01 to 0.5 nM, but the present invention is not particularly limited thereto.

The second buffer solution and the second metal precursor solution may be mixed to satisfy the R2 as described above, and the metal nanocore dispersion may be mixed so that the molar ratio of the second metal precursor and the metal nanocore is in a range of $1:1\times10^{-7}$ to $1\times10^{-5}$. In this case, the second metal precursor solution and the metal nanocore dispersion are first mixed, and the second buffer solution may then be mixed so that the metal shell can be uniformly formed on the metal nanocore(s).

Specifically, the step c) may include: c1) mixing a second metal precursor solution and a metal nanocore dispersion to prepare a precursor-nanocore mixed solution; c2) mixing a second buffer solution with the precursor-nanocore mixed solution to prepare a second reaction solution and reacting the second reaction solution at a temperature of 15 to 40° C., and favorably at room temperature for less than 20 minutes to prepare composite nanoparticles; and c3) separating and recovering the prepared composite nanoparticles, adding the recovered composite nanoparticles to a second buffer solution (i.e., a separate second buffer solution) and storing the second buffer solution at a temperature of 1 to 10° C., and particularly a temperature of 1 to 5° C.

In the step c), the composite nanoparticles, which include a metal nanocore, a self-assembled monolayer of the Raman reporter surrounding the metal nanocore, and a metal shell surrounding the self-assembled monolayer, may be prepared. In this case, the composite nanoparticles, which have an average size of 150 nm or less (i.e., a diameter calculated from a sphere having the same volume), particularly an average size of 100 nm or less, substantially a size of 40 to 100 nm, more substantially a size of 60 to 100 nm, and further substantially a size of 65 to 80 nm, may be prepared.

After the step c), the method of preparing composite nanoparticles according to one embodiment of the present invention may further include: d) fixing a receptor, which binds (specifically binds) to an analyte, in the metal shell. The step d) may be performed by mixing the receptor with the prepared composite nanoparticles dispersion. In this case, it is reasonable that the types of receptors may be fixed according to the protocols known in the art.

The receptor may be suitable as long as the receptor is any material known to form an enzyme-substrate, antigen-antibody, protein-protein, or DNA-DNA complementary bond with the analyte. In this case, the receptor may include a functional group (for example, a thiol group, a carboxyl group, an amine group, or the like) spontaneously binding to the second metal of the metal shell. In this case, the receptor may be spontaneously bound to the metal shell via the functional group.

The analyte may be a biogenic material (including viruses) or a non-biogenic material. The biogenic material may include a cell ingredient. Specifically, the analyte may be a biomaterial for labeling a lesion having lesion specificity, a pathogen, a protein, a nucleic acid, a sugar, a drug, and the like.

The analyte may be positioned in vivo, and may be detected in vivo. That is, the aforementioned composite nanoparticles may be used in vivo, and may be used for in vivo injection.

On the other hand, the analyte may be positioned in vitro, and may be detected in vitro. That is, the aforementioned composite nanoparticles may be used in vitro. In this case, the analyte may be in the form of a sample including blood, urine, a mucosal secretion, saliva, a body fluid, a tissue, a bioptic specimen, or a combination thereof, but the present invention is not particularly limited thereto.

The present invention includes the composite nanoparticles prepared by the preparation method as described above.

Hereinafter, the composite nanoparticles according to the present invention will be described in detail. In this case, in describing the composite nanoparticles, a metal nanocore, a nano-star shape, a Raman reporter, a self-assembled monolayer, a metal shell, an analyte, a receptor, and the like are similar to and the same as previously described in the method of preparing composite nanoparticles. Therefore, the composite nanoparticles according to the present invention may encompass all the same contents as previously described in the method of preparing composite nanoparticles.

The composite nanoparticles according to the present invention includes a metal nanocore having a nano-star shape; a self-assembled monolayer including a Raman reporter fixed in the metal nanocore; and a metal shell surrounding the self-assembled monolayer. The composite nanoparticles according to the present invention may not contain a surfactant. That is, the composite nanoparticles according to the present invention may be free from the organic surfactant during or right after preparation of the composite nanoparticles, and thus may have excellent biocompatibility.

The composite nanoparticles according to the present invention may include a metal nanocore having a nano-star shape.

The metal nanocore having a nano-star shape may have a central region having a size of 10 to 50 nm, and particularly approximately 10 to 40 nm, and protrusions protruding from the central region to taper in a protruding direction and having a size of 5 to 70 nm, particularly 5 to 50 nm, and more particularly approximately 10 to 50 nm. As one specific example, the nanocore may have 3 or more protrusions, and particularly 3 to 8 protrusions.

When the composite nanoparticles include the nanocore having a nano-star shape, the composite nanoparticles themselves may have a hot spot. Accordingly, the composite nanoparticles have advantages in that Raman signals may be enhanced only by the composite nanoparticles, there is no limitation on the size of the analyte, and the LSPR wavelength may be easily tuned according to the size and spherical shape of the nano-star, and thus may be tuned to a region of 800 nm. By the LSPR wavelength spanning to a region of 800 nm, it is meant that the analyte may be subjected to Raman analysis (SERS analysis) by irradiation with near-infrared rays.

Also, the composite nanoparticles according to the present invention have an advantage in that the composite nanoparticles may have uniform and stable SERS activity over the entire region of the nanocore because the Raman reporter is fixed in the nanocore in the form of a self-assembled monolayer even when the nanocore has a complex shape having very high anisotropy, which is referred to as the nano-star. Also, when the Raman reporter is positioned in the hot spot, the Raman signals may be remarkably enhanced.

In addition, the composite nanoparticles according to the present invention have an advantage in that a physically/chemically vulnerable organic component (i.e., a Raman reporter) is stably protected from external environments because the self-assembled monolayer is surrounded by the metal shell so that the self-assembled monolayer is protected by the metal shell.

Additionally, the composite nanoparticles according to the present invention have an advantage in that, when the Raman reporter has a first functional group spontaneously binding to the first metal (i.e., a metal nanocore) and a second functional group spontaneously binding to the second metal (i.e., a metal shell), the composite nanoparticles have excellent durability and stability because the nanocore, the self-assembled monolayer, and the metal shell are very strongly bound to each another.

Further, the composite nanoparticles according to the present invention may more strongly enhance the Raman signals because the nanogap (a hot spot) having a uniform size, which corresponds to the thickness of the self-assembled monolayer (corresponding to the size of the Raman reporter), is formed between the metal shell and the nanocore when the Raman reporter is fixed in the nanocore in the form of a self-assembled monolayer.

The metal shell bound to the self-assembled monolayer via the functional group (a second functional group) of the Raman reporter may be composed of fine metal particles having an average size of 1 to 5 nm. In this case, the metal shell may include irregular unevenness formed by coagulation of the fine metal particles. When a second metal serving as a material of the metal shell has a plasmon activity, an uneven structure formed by coagulation of the fine metal particles themselves and coagulation between the fine metal particles may also serve as a hot spot for enhancing Raman signals.

The composite nanoparticles may further include a receptor fixed in the metal shell to bind to an analyte, and the receptor may include a functional group spontaneously binding to the metal shell. The receptor specifically binding to the analyte may allow the analyte to be analyzed and detected by Raman spectroscopy (SERS spectroscopy), and may also allow the analyte to be sensed and bioimaged in vivo by the Raman spectroscopy (SERS spectroscopy).

The aforementioned composite nanoparticles may be used in vivo or in vitro. When the composite nanoparticles are used in vivo, the composite nanoparticles have biocompatibility. Therefore, the composite nanoparticles themselves do not need to perform separate capping, replace a surface functional group, or the like, and thus may be directly injected to the living body.

The present invention includes a SERS nanoprobe including the composite nanoparticles prepared by the preparation method as described above.

The present invention includes a SERS nanoprobe including the composite nanoparticles as described above.

FIG. 1 is a scanning electron microscope image for observing the metal nanocore prepared according to one embodiment of the present invention.

Specifically, the metal nanocore of FIG. 1 was prepared by mixing 500 μL of a $HAuCl_4$ solution (with a concentration of 40 mM) with 100 mL of a HEPES buffer solution (pH=7.2; having a concentration of 140 mM) (R1=700) and stirring the resulting mixture at room temperature and 1,000 rpm for 30 minutes. The prepared metal nanocore was stored at a temperature of 4° C. in a HEPES buffer solution having a concentration of 140 mM prior to observation of the metal nanocore followed by fixing the Raman reporter in the metal nanocore.

As shown in FIG. 1, it can be seen that the Au nanocore having a nano-star shape was prepared, and it can also be seen that the Au nanocore having a nano-star shape, which included a central region having a size of approximately 30 nm and protrusions having a length of approximately 20 to 30 nm, was prepared.

FIG. 2 is an optical image for observing the Au nanocore stored in the HEPES buffer solution. As shown in FIG. 2, it can be seen that the dispersion of the Au nanocore was stably retained without any aid of additional surfactants, organic dispersing agents, or the like.

FIG. 3 is a graph for measuring the optical absorbance of the metal nanocore prepared according to one embodiment of the present invention. In the samples of FIG. 3, $R_{[HEPES/Au]}=700$ (pH 7.2) represents an Au nanocore prepared in the same manner as in the nanocore of FIG. 1, except that the Au nanocore is prepared under the conditions in which R1 is 700 and the pH of the HEPES buffer solution is pH 7.2, $R_{[HEPES/Au]}=500$ (pH 7.2) represents an Au nanocore prepared in the same manner as in the nanocore of FIG. 1, except that the Au nanocore is prepared under the conditions in which R1 is 500 and the pH of the HEPES buffer solution is 7.2, and $R_{[HEPES/Au]}=500$ (pH 5.2) represents an Au nanocore prepared in the same manner as in the nanocore of FIG. 1, except that the Au nanocore is prepared under the conditions in which R1 is 500 and the pH of the HEPES buffer solution is 5.2.

As observed by the scanning electron microscope, it was confirmed that the lengths of the protrusions of the nano-star varied according to the R1 and the pH of the buffer solution, and the Au nanocore having a nano-star shape, which had well-developed protrusion with an increasing R1 and an increasing pH of the buffer solution, was prepared.

As shown in FIG. 3, it can be seen that, when the hot spot was formed by the protrusions protruding from the central region, the LSPR wavelength was tuned according to such a degree of development of the protrusions. Also, it can be seen that the LSPR wavelength was shifted to a longer wavelength as the protrusions were well developed. As can be seen from the $R_{[HEPES/Au]}=700$ (pH 7.2) sample, it can also be seen that the LSPR wavelength was able to be tuned to a region of near-infrared rays.

FIG. 4 is a scanning electron microscope image for observing the composite nanoparticles prepared by forming a self-assembled monolayer of the Raman reporter on the Au nanocore, followed by forming an Au shell using a HEPES buffer solution and a gold precursor solution.

Specifically, the Au nanocore (an $R_{[HEPES/Au]}=700$ (pH 7.2) sample) was recovered from a reaction solution by centrifugation (at 8,000 rpm for 10 minutes), mixed with 4 mL of a 1 mM bis(p-sulfonatophenyl)phenylphosphine (BSPP) dihydrate dipotassium salt solution, and sonicated for 10 minutes to prepare an Au nanocore dispersion with a molar concentration of 0.1 nM. 4 mL of the Au nanocore dispersion and 200 μL of 1,4-benzenedithiol (BDT) with a molar concentration of 10 mM were mixed, and the resulting mixture was sonicated for 10 minutes, and then centrifuged at 6,000 rpm for 10 minutes to recover the Au nanocore on which the self-assembled monolayer of BDT serving as the Raman reporter was formed. The recovered Au nanocore on which the self-assembled monolayer was formed was dispersed in 4 mL of deionized water (with a molar concentration of 0.1 nM), and 100 μL of 10 mM $HAuCl_4$ and 3 mL of a 100 mM HEPES buffer solution (pH 7.2) were added to the dispersion, and stirred for 10 minutes to prepare the composite nanoparticles as shown in FIG. 4. In this case, the R2 was 300.

As shown in FIG. 4, it can be seen that the entire region of the nano-star including the protrusions was stably surrounded by the fine Au particles having surface unevenness formed therein by means of coagulation, and the composite nanoparticles in the form of popcorn having an uneven surface were prepared. From the lower panel of the image of FIG. 4 observed under the high-magnification scanning electron microscope, it can also be seen that the fine Au particles having a size of several nanometers coagulated to form irregular surface unevenness.

FIG. 5 is a graph showing the surface-enhanced Raman scattering (SERS) spectrum of the prepared composite nanoparticles (a sample of FIG. 4). The SERS spectrum was obtained by irradiating the composite nanoparticles with light of 514 nm, 633 nm, or 785 nm using a Micro Raman system (Horiba).

As shown in FIG. 5, it can be seen that the very strong Raman scattering signals were obtained by light having a near-infrared band of 785 nm, and also that the strong Raman signals observed in the vicinity of a 1,100 $cm^{-1}$ region and 1,550 $cm^{-1}$ region were coincident with the innate SERS signals of the Raman reporter (DBT).

Although the subject matters of the present invention have been described in the present invention with reference to certain subject matters and limited examples thereof and the accompanying drawings, it should be understood that the subject matters and limited examples described herein are provided to aid in understanding the present invention more comprehensively, but are not intended to limit the present invention. Therefore, it will be apparent to those skilled in the art to which the present invention belongs that various modifications can be made from the detailed description of the present invention.

Thus, the scope of the present invention is not intended to be limited to the examples described herein, and thus all types of the appended claims, and equivalents or equivalent modifications thereof fall within the scope of the present invention.

The invention claimed is:

1. A method of preparing composite nanoparticles, comprising:
   a) preparing a metal nanocore having a nano-star shape from a first reaction solution in which a first metal precursor is mixed with a first buffer solution;
   b) fixing a Raman reporter in the metal nanocore; and
   c) forming a metal shell, which surrounds the nanocore in which the Raman reporter is fixed, from a second reaction solution in which the nanocore in which the Raman reporter is fixed, and a second metal precursor are mixed with a second buffer solution.

2. The method of claim 1, wherein each of the first reaction solution and the second reaction solution does not contain a surfactant.

3. The method of claim 1, wherein a shape, a size, or both the shape and the size of the nanocore is adjusted by controlling one or more factors selected from a molar ratio of the first metal precursor to a first buffer agent of the first buffer solution; and a pH of the first buffer solution.

4. The method of claim 3, wherein a molar ratio R1 obtained by dividing the number of moles of the first buffer agent by the number of moles of the first metal precursor is in a range of 200 to 750.

5. The method of claim 1, wherein a molar ratio R2 obtained by dividing the number of moles of the second buffer agent of the second buffer solution by the number of moles of the second metal precursor is in a range of 100 to 400.

6. The method of claim 1, wherein each of the first buffer solution and the second buffer solution contains one or more selected from 4-(2-hydroxyethyl)-1-piperazineethane sulfonic acid (HEPES), 4-(2-hydroxyethyl)piperazine-1-ethane sulfonic acid (MES), phosphated buffered saline (PBS), tris(2-amino-2-hydroxymethyl propane-1,3-idol), phosphate buffer (PB), 3-(N-morpholino)propane sulfonic acid (MOPS), 3-[[1,3-dihydroxy-2-(hydroxymethyl)propan-2-yl]amino]propane-1-sulfonic acid (TAPS), and piperazine-N,N'-bis(2-ethane sulfonic acid) (PIPES).

7. The method of claim 1, wherein a metal of the metal precursor is Au or Ag.

8. The method of claim 1, further comprising, after the forming of the metal shell from the second reaction solution:
   d) fixing a receptor, which binds to an analyte, in the metal shell.

9. The method of claim 1, wherein the composite nanoparticles are used in vivo.

* * * * *